(12) United States Patent
Del Rio et al.

(10) Patent No.: US 8,939,979 B2
(45) Date of Patent: Jan. 27, 2015

(54) SURGICAL DRILL WITH CURVED BURR ATTACHMENT AND METHOD

(75) Inventors: Eddy H. Del Rio, Royal Palm Beach, FL (US); Douglas A. Perry, Palm Beach Gardens, FL (US)

(73) Assignee: DePuy Synthes Products, LLC, Raynham, MA (US)

( * ) Notice: Subject to any disclaimer, the term of this patent is extended or adjusted under 35 U.S.C. 154(b) by 645 days.

(21) Appl. No.: 12/387,838

(22) Filed: May 8, 2009

(65) Prior Publication Data

US 2010/0286694 A1 Nov. 11, 2010

(51) Int. Cl.
  *A61B 17/16* (2006.01)
  *A61B 17/00* (2006.01)

(52) U.S. Cl.
  CPC ........... *A61B 17/1631* (2013.01); *A61B 17/162* (2013.01); *A61B 17/1679* (2013.01); *A61B 17/1688* (2013.01); *A61B 2017/00738* (2013.01)
  USPC ............................................. 606/80; 606/79

(58) Field of Classification Search
  USPC ............................................. 606/86 R, 7–85
  See application file for complete search history.

(56) References Cited

U.S. PATENT DOCUMENTS

| | | | | |
|---|---|---|---|---|
| 2,725,495 A | * | 11/1955 | Rively | 313/38 |
| 3,867,943 A | * | 2/1975 | Nordin | 606/180 |
| 4,265,231 A | * | 5/1981 | Scheller et al. | 606/80 |
| 4,686,982 A | | 8/1987 | Nash | |
| 4,811,736 A | | 3/1989 | Griggs et al. | |
| 5,271,697 A | * | 12/1993 | Johnson et al. | 408/222 |
| 5,358,509 A | * | 10/1994 | Fine et al. | 606/180 |
| 5,505,737 A | * | 4/1996 | Gosselin et al. | 606/79 |
| 5,741,263 A | * | 4/1998 | Umber et al. | 606/80 |
| 5,928,241 A | * | 7/1999 | Menut et al. | 606/80 |
| 7,604,636 B1 | * | 10/2009 | Walters et al. | 606/80 |
| 2002/0151902 A1 | * | 10/2002 | Riedel et al. | 606/80 |
| 2005/0177168 A1 | * | 8/2005 | Brunnett et al. | 606/80 |

(Continued)

OTHER PUBLICATIONS

U.S. Official Action, dated Dec. 14, 2012, received in connection with related U.S. Appl. No. 12/387,828.

(Continued)

*Primary Examiner* — Matthew Lawson
*Assistant Examiner* — Zade Coley
(74) *Attorney, Agent, or Firm* — Meunier Carlin & Curfman, LLC (57) ABSTRACT

A surgical drilling instrument with a Curved Burr Attachment having an adapter removably coupled to a drill motor and a burr attachment coupled to said adapter. The burr attachment includes a tube with a wire shaft supported therein and a coil wire surrounding said wire shaft and having each of the coils touch the outer periphery surface of the wire shaft and the inner peripheral surface of said tube to enhance cooling of said outer periphery of said tube from the heat generated by said wire shaft and attenuate vibrations while allowing said burr attachment to be bent without kinking. The burr attachment includes a proximal end support and a distal end support formed on the end of said burr attachment wherein the wire shaft is affixed to said proximal end support and rotates relative to said distal end support and includes detents formed on each of the supports for engaging balls in said adapter so as to be operatively connected thereto when the burr attachment is aligned in said adapter to couple the burr attachment to said adapter for rotary motion of said wire shaft and locating the cutter of said burr attachment to a precise location relative to the end of the adapter. The burr attachment being disposable and the adapter being re-usable.

17 Claims, 7 Drawing Sheets

(56) References Cited

U.S. PATENT DOCUMENTS

2006/0229624 A1 10/2006 May et al.
2006/0241630 A1 10/2006 Brunnett et al.
2008/0306334 A1 12/2008 Okada

OTHER PUBLICATIONS

U.S. Official Action, dated Jan. 19, 2012, received in connection with related U.S. Appl. No. 12/387,828.

* cited by examiner

SURGICAL DRILL WITH CURVED BURR ATTACHMENT AND METHOD

RELATED APPLICATIONS

This invention relates to U.S. patent application Ser. No. 12/387,828, entitled BURR ATTACHMENT filed May 8, 2009, by the same inventors and assigned to the same assignee.

FEDERALLY SPONSORED RESEARCH OR DEVELOPMENT

Not applicable

TECHNICAL FIELD

This invention relates to a surgical cutting instrument (Curved Burr Attachment) and particularly to a portable and disposable burr attachment with the ability to utilize different sized ball cutters primarily used for cutting bone and being capable of changing the angle of the attachment to different angles to fit into minute curved portions of the anatomy, as for example, the middle ear, although this surgical drill can be utilized for other surgical procedures. For example, this invention can be utilized in surgical procedures such as otological surgery, cochleostomies, removal of acoustic neuroma tumors, removal of the scutum in a tympanoplasty, cochlear implant, ossicular chain reconstruction, drainage of petrous apex cyst, amstoidectomies, amongst others.

BACKGROUND OF THE INVENTION

This invention is particularly efficacious because it provides a good feel to the surgeon (user friendly), it provides significant visibility of the surgical sight, the attachment is bendable at-will without kinking to afford easy access to the target, enhances visibility, it is rigid and avoids any distortions and wobbling of the cutter, it operates at a high speed (RPM), say, 80,000 to 90,000 RPM, it provides heat dissipation, a unique lubrication technique and it is disposable. It is paramount that a medical instrument or component that is disposable should be cost effective. What is meant by disposable in the context of this patent application is that the attachment, namely, the burr and its supporting structure (burr attachment) are detachable from the drill motor and the adapter and is disposable. In the prior art, for example, the burr and its extensions are made integral with the adapter (sometimes referred to as the clutch or clutching mechanism) so that in order to make the burr disposable, the adapter, being attached thereto, is, of necessity, also disposable. It is readily understood that this is a less desirable scenario because it is less cost effective.

A good example of the differences between a more cost effective disposable component and a less cost effective disposable component is a comparison with the present invention and the instruments disclosed in the US Publication No. 2005/0177168 invented by Brunett, et al and entitled HIGH SPEED SURGICAL CUTTING INSTRUMENT (which is incorporated in its entirety herein by reference). In the present invention the comparable medical instrument is comprised of a motor, an adapter and the Curved Burr Attachment which is essentially the same elements of the instrument disclosed in the Publication, although the terminology is different. The elements in the instrument disclosed in the Publication, supra, that compares to the Curved Burr Attachment is the wire and the cutter extending at the end of the wire and its support structure, the chuck mechanism and the motor. Since the wire/cutter and support mechanism also includes an integral chuck mechanism (comparable to the adapter of the present invention) that serves to connect to the motor, the disposable portion includes both the wire/cutter and its support mechanism, as well as the clutch mechanism. In contrast, the present invention merely disposes the burr attachment of the Curved Burr Attachment instrument and hence, the remaining portion of the instrument, namely, the adapter (the more expensive portions of the tool) are re-usable. Obviously, every portion of the tool may be disposable, but this is impractical to do because of the cost and obviously, the drill motor is a capital investment and has many uses. What the industry needs and desires is a tool, of this type, which is extremely small, (ball cutters range in 0.5 mm-2 mm) which includes a disposable burr that is substantially inexpensive and hence, cost effective.

This type of medical instrument, because of its size and speed that is required to perform certain medical procedures, under normal operational circumstances, it is limited to the amount of time it can be placed in continuous use. Under medical practices, it is well known that the surgeon in most instances typically perform a surgical procedure under a minute. This invention provides at least 2 minutes of continuous operation where the heat generated at the cutter will not adversely affect the nerves and other parts of the patient's anatomy.

This invention constitutes an improvement over the surgical instrument that is disclosed in U.S. Pat. No. 4,811,736 granted to Griggs et al on Mar. 14, 1989 and entitled SURGICAL DRILL AND BUR FOR USE THEREWITH and also being incorporated herein in its entirety by reference. This invention, like the structure disclosed in the '736 patent, supra, is intended to be utilized in performing, amongst other types of surgery, otological surgery. While the surgical drill of the '736 patent, supra, may be highly viable, it is limited in the potential available rotational or cutting speed, particularly, because it utilizes a plastic sleeve (journal) bearing. According to the patentee of the Publication, supra, the operational speed of the structure disclosed in the '736 patent, supra, is "less than 20,000 RPM." The present invention is intended for use where the RPM is typically in the 80,000 range. Furthermore, like the differences between the structure disclosed in the Publication, supra, the present invention is completely different from the structure in the '736 patent, supra, and affords features that are not taught in this reference patent.

The aforementioned Publication, supra, is worthy of mention because, in addition to the features disclosed therein, the present invention includes features, that are unobvious and novel, and that constitute an improvement there over. As mentioned above, the Publication, supra, describes a cutting tool that is intended for surgical use for the same types of surgical procedures that are intended for use by the present invention. As disclosed therein the medical instrument describes structure that includes a cutting instrument assembly having a support tube, an inner wire assembly (bur), a cutting tip, a coupling chuck within a housing and a motor (not shown) for rotating the cutting tip. The present invention, while using different names, provides a motor, an adapter and the burr with a cutting tip, which is terminology that applies to both structures, albeit, that the present invention is designed differently than what is disclosed in the Publication, supra, The features of the present invention are, namely, without limitations, the Curved Burr Attachment which is disposable, it provides an enhanced thermal effectiveness, includes a lubrication delivery system and is bendable at-will by the operator without adverse effects. What this means is that the attachment may be bent in a normal or customary acceptable curvature at the factory, while also providing to the operator the option of changing the bend or angle of the attachment at-will while still maintaining the rigidity and structural integrity of the assembly. The present invention also provides to the user a medical instrument that is capable of being utilized a significant length of time to perform a particular operation because of the heat dissipation. And the Curved Burr Attachment is the only portion of the medical instrument that is disposable. This latter feature is an important distinction over the prior because no other component has to be disposed other than the disposable Curved Burr Attachment. Obviously. This makes the unit cost effective and leaves the more costly capital expenditures, the adapter, to be re-used. Hence, these features just described and that are afforded by the present invention are in addition to the features described in the Publication, supra, namely, high-speed operation with minimal impact of user visibility, minimized heat-build-up, and improved stiffness.

The following is an explanation to show and support the fact that the specific differences between the disposable portions of the present invention and the ones described in the Publication, supra. Referring to the Publication, supra, itself, it states that "The coupling chuck is secured to the proximal section of the inner wire assembly. To this end, the coupling chuck is adapted for coupling to a drive mechanism of a drill." In comparison with the present invention, in the present invention the "coupling chuck" is referred to as an "adapter" and the wire assembly is referred to as "burr". What is significant is that in the structure of the Publication the coupling chuck and wire assembly are united and form an integral unit and are un-separable after assembly. This means that for it to be disposable this entire unit would have to be disposed. In the present invention, the adapter and burr and its attendant hardware are separate items and the burr is removable from the adapter such that it is the only portion of the inventive surgical instrument that is disposable, resulting in a cost effective device. Obviously, in the present invention the adapter is re-usable for future use, as will be described in detail in the description to follow.

In addition to the aforementioned features of the present invention, namely, the ability to bend the burr at-will, and the burr being disposable in a cost effective manner, the particular manner in which lubrication is applied to the burr is unique. In the present invention the wire-shaft of the burr is surrounded by a coil wire that extends to approximately from the proximal end to the distal end of the wire-shaft and is oriented in such a manner that the helix formed by the coil wire is in a upward direction so that by placing grease at the distal end, the rotation of the wire-shaft causes the grease to migrate from the distal end to the proximate end, namely, in the upward direction.

In addition to the lubrication feature and the bending without the kinking feature of the present invention, the coil wire which is fixed and non-rotatable, also serves another function, i.e. it dissipates heat. This is accomplished by judiciously locating the coil wire between the inner wall of the support sleeve or tube of the burr and the wire-shaft such that the outer and inner edges of each coil touches both the side of the inner wall of the support sleeve and the outer periphery of the wire-shaft, respectively. This serves to conduct the heat away from the wire-shaft and from internally of the support sleeve. Distributing the heat dissipation load in this manner reduces the heat or slows down the heat at the cutter resulting in additional time that the Curved Burr Attachment can be in continuous use in a medical procedure. As one in this technology knows the heat generated by the cutter can adversely affect nerves and other portions of the anatomy.

Another function of the coil wire is that it permits the bending of the burr without causing kinking. In accordance with this invention, the burr attachment of the Curved Burr Attachment is bent at the factory and may be, at the option of the surgeon, bent at-will.

SUMMARY OF THE INVENTION

An object of this invention is to provide an improved high speed surgical drill with a disposable and bendable burr attachment.

Another object of this invention is to provide an improved high speed surgical drill characterized by being high-speed operation with minimal impact of user visibility, minimized heat-build-up, lubrication technique, enhanced time in use during medical procedure, and improved stiffness characteristics.

A feature of this invention is to provide a coil wire that wraps around the wire-shaft of the burr such that it prevents kinking when the Curved Burr Attachment is bent and it serves to provide heat transfer from the wire shaft to the inner diameter of the support tube surrounding the coil wire and provides a means for migrating grease from the distal end of the support tube upwardly toward the proximal end for lubricating the wire-shaft.

Another feature of this invention is the inclusion of key slots for both the rotating and non-rotating portions of the Curved Burr Attachment that complement keys formed on the rotating and non-rotating portion of the Curved Burr Attachment instrument for accepting the burr attachment.

Another feature of this invention is to provide mechanism for locking the burr attachment in place when inserted into the adapter and orienting it so that the cutting member is in the exact proper position.

Another feature of this invention is that the adapter is re-usable.

The coil wire is seated and placed in position by an upper and lower seat formed in the members attached to the tube support member.

The burr attachment of the Curved Burr Attachment instrument is intended to be bent in the optimum position at the factory with the option of being capable of being further bent at the will of the surgeon and the bent can be made without the incidence of kinking.

The foregoing and other features of the present invention will become more apparent from the following description and accompanying drawings.

DETAILED DESCRIPTION OF THE INVENTION

Figure 1:
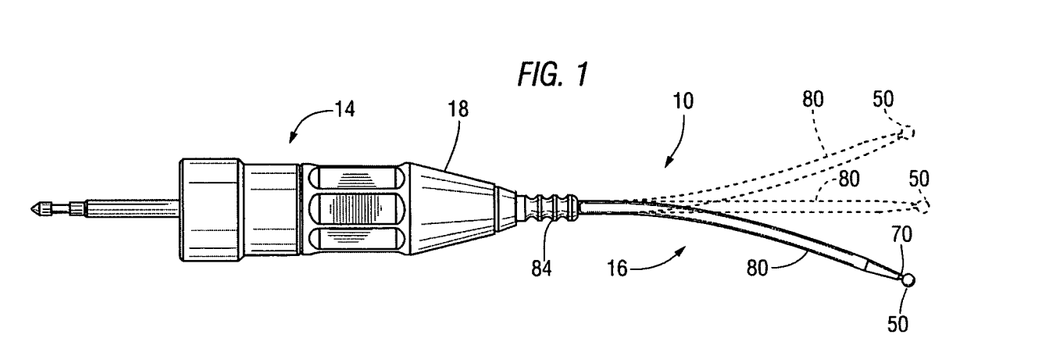
FIG. 1 is a view in elevation and phantom illustrating the present invention of the burr attachment attached to the adapter and illustrating the various positions that the instrument can be bent into.
Figure 2:
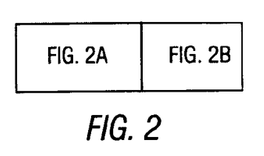
FIG. 2 is a sectional view of the invention depicted in FIG. 1 and including in a phantom view the motor attached to the adapter for rotating the burr attachment of this invention.
Figure 2A:
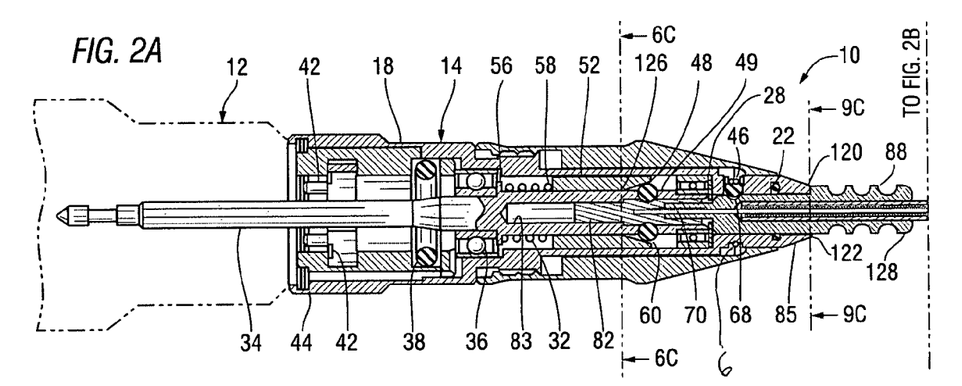
Figure 2B:
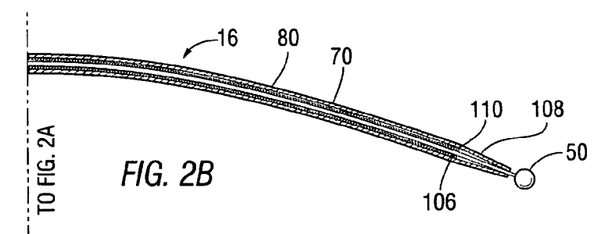

As best seen in FIGS. 1 and 2, this invention is a high speed (80,000 RPM-90,000 RPM) surgical instrument particularly efficacious for operating on small bones as for example, those found in the ear, nose and throat area, although not restricted thereto and generally illustrated as reference numeral 10 comprising a motor 12 (shown in phantom), an adapter 14 and the burr attachment 16 with the capability of being bent as shown in phantom and the burr attachment being disposable as will be described in detail herein below. While the particular motor used to rotate the drilling burr is of no moment, the X-Max® series or the E-Max® series, pneumatic and electric motors, respectively, are contemplated for use with this invention and are commercially available from the assignee of this invention, namely, The Anspach Effort, Inc of Palm Beach Gardens, Fla. 33410.

Figure 3:
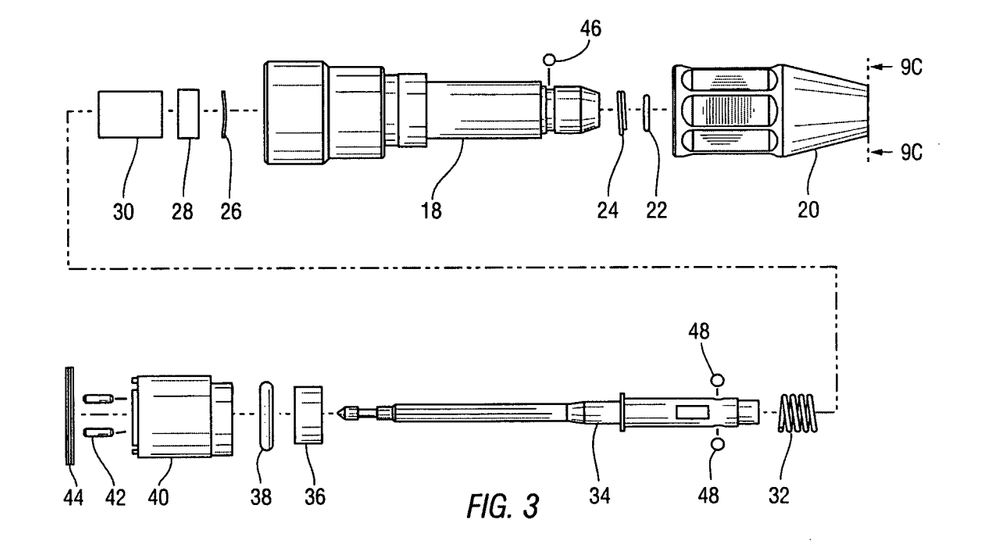
FIG. 3 is an exploded view of the adapter of the Curved Burr Attachment instrument depicted in FIG. 1.
Figures 4, 4A:
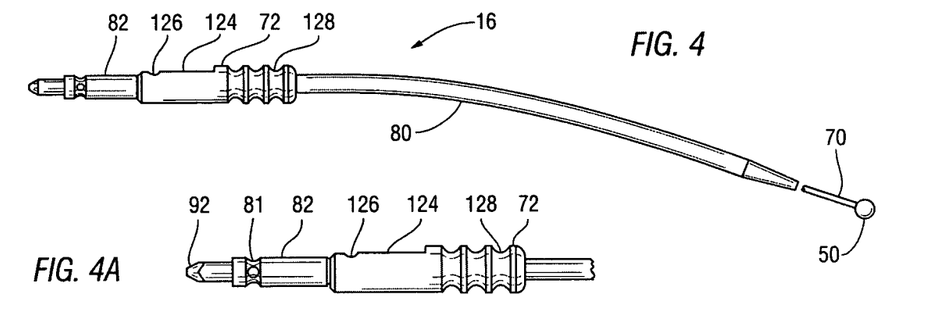
FIG. 4 is a perspective view of the burr attachment for the Curved Burr Attachment instrument of this invention.
FIG. 4A is a fragmentary enlarged view in perspective illustrating an elevation of the burr attachment depicted in FIG. 4.
Figure 4B:
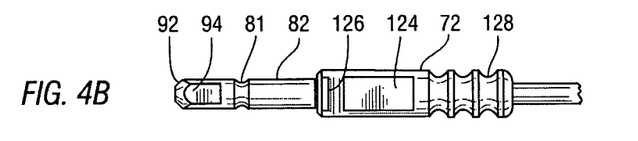
FIG. 4B is a fragmentary enlarged view in perspective illustrating a plan view of the burr attachment depicted in FIG. 4A.

The adapter 14 of this invention is best seen in FIGS. 2 and 3 comprising the main housing 18, the detent spring cover 20, O-ring 22, spring ring 24, wave washer 26, bearing 28, ball retainer 30, spring 32, spindle 34, bearing 36, O-seal 38, bushing and motor coupling 40, pin 42, retaining ring 44, ball 46 and ball 48 (FIG. 3). The motor 12 serves to power the Curved Burr Attachment instrument by providing rotary movement to the burr cutter which is essentially a spherical ball that is diamond coated or fluted and well known in this technology. Attached to the motor by a suitable and well known chuck (not shown and available from The Anspach Effort, Inc., supra) is the adapter 14 and connected to the spindle 34 for rotating the same. Spindle 34 is supported in the main housing 18 by the bearing 36 and bearing 28. Sandwiched between the inner surface of the main housing is sleeve/cam 52 having bevel edge 54 formed on the inner diameter thereof. Spring 32 disposed between shoulder 56 and the proximal end 58 of the sleeve/cam 52 biases the sleeve/cam 52 toward the distal end so that the sleeve/cam 52 engages the balls 48. Balls 48 fit into a circular hole and engage the cam surface 60 of the sleeve/cam 52 at a judicious location at the proximal end of the burr attachment 16. When the balls 48 are in engagement, the balls are forced against the peripheral surface of the proximal which serves to rotate the cutter wire shaft 70 and burr cutter 50 as will be described in further detail herein below. O-seal 38 mounted at the proximal end at the juncture between the bushing motor coupling 40 and main housing 18 and O-seal mounted in the distal end of the main housing 18 serve to assure that the inside of the adapter 14 remains clean and free from foreign matter.

Also nested in the main housing 18 is ball 46 biased radially inward by the spring ring 6 to engage detent 68 formed on the distal end support of the burr attachment 16. This serves to define the position of the burr cutter 50 relative to the Curve Burr Attachment instrument when the burr attachment 16 is inserted into the adapter 14. In other words, the relative position of the cutter 50 will be determined by the position of the ball 46 when in its detent 68, which will be described in further detail herein below.

The disposable burr attachment 16 of the Curved Burr Attachment instrument will be described next and reference should be made to FIGS. 4 through 10. As noted from these Figs., the burr attachment 16 comprises the wire shaft 70, and attached cutter 50, the tube 80 defining the outer support for the burr attachment 16, and proximal end support 82, distal end support 72, coil wire 86 and nose cap 108. All the elements of the burr attachment are made from a surgical steel or other suitable material where the hardness and tensile strength of the wire shaft 70 and attached cutter, the tube 80, proximal end support 82, distal end support 72 and nose cap 85 are higher than the hardness and tensile strength of the coil wire 86. (Unlike a spring the coil wire does not exhibit any spring-like characteristics) These parameters are selected to assure that the burr attachment is sufficiently rigid to support the high rotational speed, yet sufficiently malleable to be hand bent without incurring any kinking.

As alluded to in the above paragraphs, the burr attachment 16, and only the burr attachment 16, is disposable. Hence, this invention assures that the burr attachment 16 is both easily inserted into the adapter and easily removed. To this end, the operator must be able to easily put the end of the burr attachment 16 into the passageway or central bore 83 with the burr attachment 16 being oriented so that the coupling between the adapter and the burr attachment are mated (ball 48 fits into annular groove 81) and that the burr attachment 16 aligns with the adapter (ball 46 fits into detent 68) so that when the burr attachment 16 is locked into place the cutter 50 is in its exact position relative to the distal end of adapter 14 to assure that the instrument is exacting and precise for use by the surgeon. As noted in FIGS. 4A, 4B, 6A, 6B and 6C, the distal end support 82 is comprised of a main generally cylindrical body 90 with an annular groove 57 formed intermediate the ends thereof, a generally tapered end 92 and a flat portion 94 formed on the peripheral surface of the main body 90. The tapered end 92 is not symmetrical but rather is asymmetrical and tapered to match the inlet opening 96 formed at the entrance 87 of the central bore 83. Hence, the shapes of the entrance and the tip of the proximal end support 82 serve as a key and key slot such that the proximal end support 82 can fit into the central bore 83 in only one position. Internally of the proximal end support 82 includes a central passage or partial bore 100 and a wider diameter partial bore 102, The smaller bore 100 receives the end of the wire shaft 70 which is suitably fitted to form an integral unit, say by shrink fitting, swaging or the like, so that in operation the proximal end support 82 and wire shaft 70 rotate together as a unit. The distal end support 72 and the proximal end support 82 are joined together through the reduced diameter portion 123 formed on the end of distal end support 72 that fits into the larger diameter slot 102 formed on the proximal end support 82 and these elements are dimensioned to allow the proximal end support 82 and wire shaft 70 to rotate while the distal end support 72 remains fixed, as will be described in more detail herein below.

Figure 9:
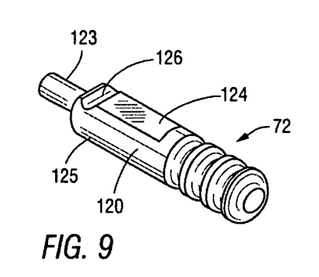
FIG. 9 is a perspective view of the distal end support of the burr attachment of this invention.
Figure 9A:
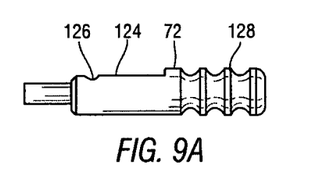
FIG. 9A is a side view in elevation illustrating the distal end support depicted in FIG. 9.
Figure 9B:
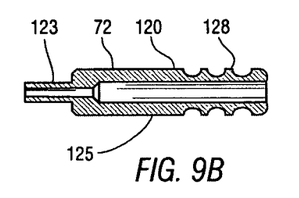
FIG. 9B is a sectional view of the distal end support depicted in FIG. 9.
Figure 9C:
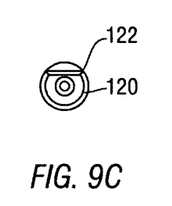
FIG. 9C is an end view of the tip at the distal end of the adapter taken along lines 9C-9C depicted in FIGS. 2 and 3.
Figure 10:
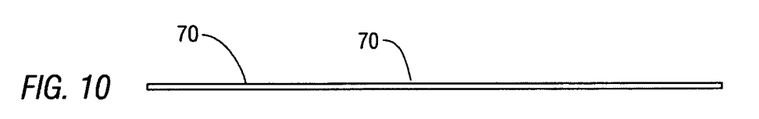
FIG. 10 is a view in elevation illustrating the burr cutter and shaft for use with this invention.

It is important and in accordance with this invention that the distal support end 72, as best seen in FIGS. 9, 9A and 9B, is properly oriented when inserted into the adapter 14, so that the wire shaft 70 and cutter 50 (representing all the different sizes used by this medical instrument) are always in the exact same position relative to the distal end of adapter 14. To this end, the main body 120 of the distal support end 72 is generally cylindrical in shape and includes a large diameter portion 125, a smaller diameter portion 123. The smaller diameter 123 portion fits into the end of the proximal end support 82 as was discussed above. Each unit is oriented relative to each other so that the flat portion 94 lies in the same plane as the flat portion 124 formed on the inner periphery of the nose cap 85 of adapter 14. Groove 126 formed adjacent to the flat portion 124 serves to receive ball 46 which, in turn, serves to position the cutter 50 relative to the end of the nose cap 108. The foreward portion of the main body 120 includes a serrated or grooved portion 128 that serves as a grip for the surgeon to remove the burr attachment from the adapter. Obviously, any type of grip, such as a knurl, can be used without departing from the scope of this invention.

Coil wire 86 fits between the spring seat 104 and the seat 106 formed on the proximal end 110 of the nose cap 85. When the coil wire 86 is installed into the tube 80 each end thereof bears against the coil wire seat 104 and the coil wire seat 106 and the insertion of the nose cap 108 is dimensioned so that it holds coil wire 86 in place. This assures that coil wire 86, surrounding the rotating wire shaft 70, remains fixed. It will be noted that coil wire 86 is tightly wound and essentially serves as a journal bearing for the wire shaft 70.

It will also be noted and in accordance with this invention that the helix orientation of the coils of coil wire 86 are in a direction that looking at FIG. 2 are from left to right or looking at the bottom they are in a clockwise direction. The direction of the helix serves to flow grease in the upward direction toward the proximal end. Because of the orientation of the coils, the grease inserted at the distal end of the unit in the clearance between the wire shaft 70 and inner diameter of the nose cap 108 into the tube 80 lubricates the entire the wire shaft 70.

Figure 5:
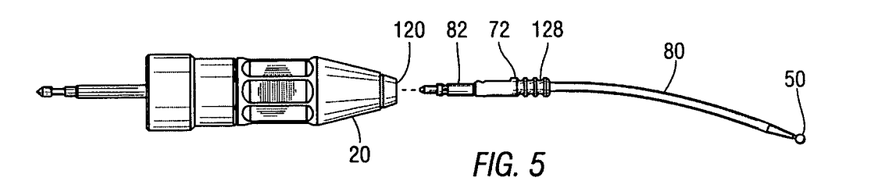
FIG. 5 is an exploded view in perspective illustrating the disposable and bendable burr attachment and the adapter combination of the Curved Burr Attachment instrument.
Figure 5A:
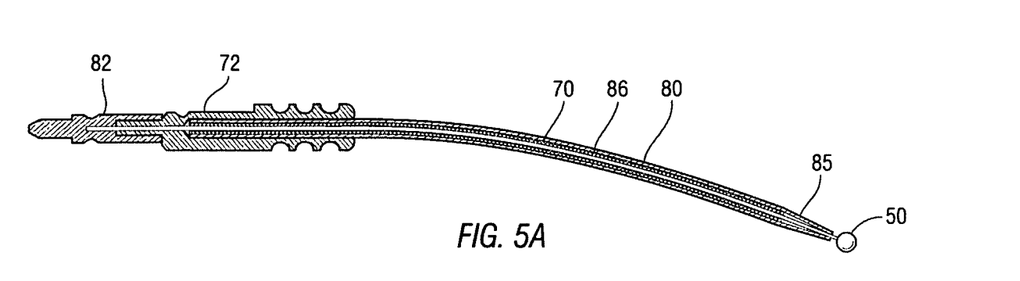
FIG. 5A is a sectional view of the burr attachment depicted in FIG. 5.
Figure 5B:
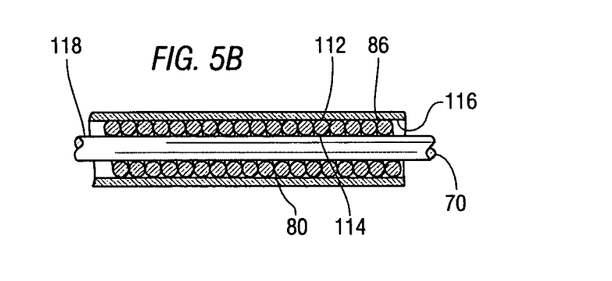
FIG. 5B is an enlarged fragmentary view of the tube, wire shaft and coil wire depicted in FIG. 5.
Figure 6:
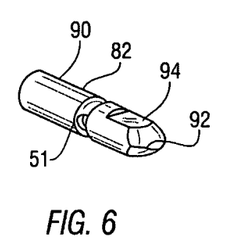
FIG. 6 is a perspective view of the burr attachment proximal end of this invention.
Figure 6A:
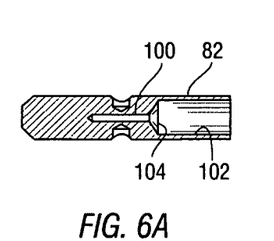
FIG. 6A is a sectional view of the burr attachment proximal end depicted in FIG. 6.
Figure 6B:
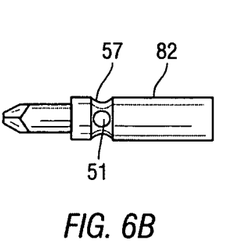
FIG. 6B is a side elevation view of the burr attachment proximal end depicted in FIG. 6.
Figure 6C:
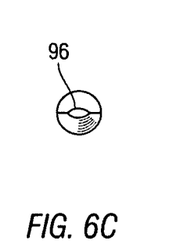
FIG. 6C is an end view taken along lines 6C-6C of the adapter depicted in FIG. 2 illustrating the entrance to the passageway into the adapter for admitting the burr attachment proximal end depicted in FIG. 6B.
Figure 7:
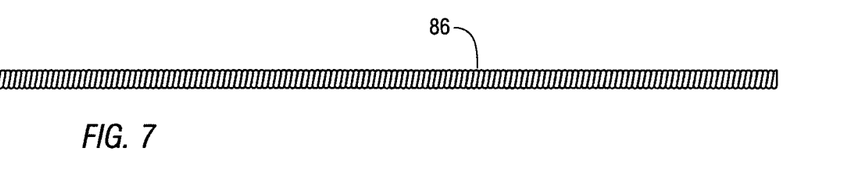
FIG. 7 is a view in elevation illustrating the coil wire of this invention.
Figure 8:
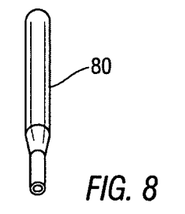
FIG. 8 is a view in perspective illustrating the tube support structure for the burr attachment.
Figure 8A:
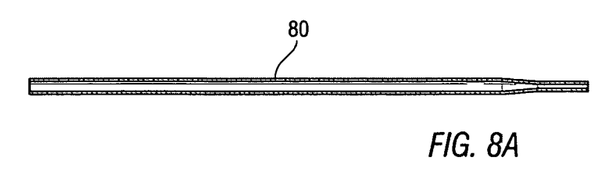
FIG. 8A is a sectional view of the tube depicted in FIG. 8.

It will also be noted and in accordance with this invention, as evidenced in FIG. 5B, that the peripheral top and bottom surfaces 112 and 114 of each coil wire 86 touch, by a point contact, the inner diameter surface 116 of tube 80 and the outer surface 118 of wire shaft 70 and this connection serves to minimize the heat transfer through the coil wire 86 and tube 80. This minimizing of the heat transfer of shaft 70 serves to keep the outer tube 80 cooler than it would otherwise be without this feature. It wilt be obvious to the skilled artisan that the wire shaft 70 is notably supported by the coil wire 86 and that for rotation to be effective that is a minimal space between the wire shaft 70 and coil wire 86 where lubricant can be placed. Hence the point contact of the coils of the coil wire 86 is random that occurs as the shaft rotates around 80,000 to 90,000 rpm. The importance of maintaining the outer surface of tube 80 cooler by virtue of this heat transfer feature of this invention the operational time of the Curved Burr Attachment is enhanced. In addition, because of the coil wire 86 location, namely, by the touching of the wire shaft 70 and of the inner surface of tube 80, vibration of the Curved Burr Attachment is minimized.

In operation of the medical instrument, when the adapter is coupled to a motor, the surgeon will insert the burr attachment into the adapter by orienting the proximal end support 82 so that the flat portion 94 aligns with the secanted portion 122 formed in the opening 120 of the adapter 14. Obviously the surgeon may have to rotate the burr attachment 16 until the flat portion 94 which serves as the key aligns with the secanted portion 122 defining a key slot formed at the entrance of the adapter 16. Once aligned, the surgeon merely pushes the burr attachment 16 into the adapter 14 where the tapered asymmetrical end 92 fits into the key slot 96 formed at the entrance of the central bore 83. In order to permit the burr attachment 16 to reach the end of the adapter and into its operating position, the cam 52 must detach from the balls 48 which would initially be in the contact position shown in FIG. 2. This invention has a unique design for accomplishing this task. As one skilled in this art appreciates, there are ball locking mechanism available in the prior art, as for example, key chains and others, which include both a ball and detent. However, in all these designs, an actuator must be engaged to allow the positioning of the cam to become detached from the ball. In accordance with this invention, no external actuation mechanism is utilized and the locking feature merely requires the insertion of the burr attachment 16, which obviously is a very simple, uncomplicated operation. To this end, the movement of the burr attachment 16 into the adapter 14 causes shoulder 126 and the balls 48 resting in the slot 57 of the proximal end support 82 to bear against the end surface of sleeve like cam 52 which, in turn, forces the cam 52 rearward against the force of the spring 32. This movement causes spring 32 to compress. The spring rate of spring 32 is selected such that the cam 52 will move rearward until the spring compresses a sufficient distance which creates a force on the spring so that its value reaches a point where the force of the spring will now drive the cam toward the distal direction and back to its original position. As is evident from the drawing (FIG. 2) the proximal end support 82 reaches its maximum position and the shoulder 126 bears against the shoulder 128 formed internally of spindle 34. At this juncture the force of spring 32, as noted above, urges the cam 52 toward the distal end so that the bevel portion 60 drives the balls 48 radially inwardly to fit into the aligned annular groove 57. (Hole 51 serves to receive a tool to swage the proximal end support to the wire shaft 70 of the burr attachment). This connection couples the spindle to the proximal end support 82 as well as the wire shaft 70 which is connected thereto so as to impart rotary motion thereto. Obviously, the motor 12 being suitably attached to the adapter to drive the spindle 34 and the adapter 14, in turn, will drive the cutter 50 to now rotate at the desired rotational speed, say 80,000 RPM and become ready for the surgeon to perform the medical procedure. It will be appreciated that the cutter 50, as described above, is in the precise operating position because the ball 46 of the adapter 14 aligns with the slot 126 formed in the distal end support 72.

The removal of the burr attachment is a simple operation where the surgeon merely pulls on the grip 128 and pulls the burr attachment 16 outward to remove the same. The balls 48 in this instance are moved toward the distal end of the burr attachment 16 into the space formed at the distal end of cam 52. Since the balls 48 have room to move radially outward, the proximal end support 82 of the burr attachment 16 can proceed toward the distal end. The other ball 46 is spring loaded radially inward and the movement merely forces this ball 46 radially outward, allowing the burr attachment 16 to progress out of the adapter 14. Obviously, the consequence of this design is that the removal of the burr attachment 16 is simple and at this point the burr attachment 16 may be discarded, leaving the adapter for future use.

It will be appreciated that in certain operations, particularly affecting the ear, the surgeon may have to re-adjust the angle of the burr attachment. Since the coil wire 86 is mounted between the tube 80 and wire shaft 70, the surgeon can bend the burr attachment to any desired angle to suit the particular operation being performed. Because of this design, the burr attachment 16 will not kink and will leave a smooth bend and yet the tube and wire shaft will provide sufficient rigidity to perform the rotation in a precise manner.

Figure 11:
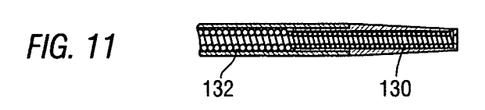
FIG. 11 is a fragmentary view illustrating another embodiment of this invention.

FIG. 11 discloses another embodiment and is identical to the burr attachment 16 save for inserting a double coil wire to replace coil wire 86 (like reference numerals represent like parts in all the embodiments). Obviously, the larger coil wire 132 that is located where the bend occurs, serves to strengthen the burr attachment 16, and the rigidity and the bending thereof. As seen in FIG. 11 a smaller coil wire 130 surrounds the wire-shaft (not shown) and fits against the inner surface of the tube 80 and extends a portion into the burr attachment 16. The larger coil wire 132 whose helix is oriented in the same direction as the smaller coil wire 130, continues the remaining distance so that the coil wires when assembled are held in a place, similarly to the design of the other embodiment. It will be noted, as in the case of the other embodiment, the orientation of the helix allows the lubrication of the wire-shaft in the same manner as in the previous embodiment, namely, merely by placing grease or the like at the entrance of the burr attachment 16, the rotation of the wire shaft will cause the lubricant to migrate upwardly into the burr attachment 16 to lubricate the entire wire shaft.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A medical instrument for burring into small bones in a human patient comprising,
    an adapter coupled to a motor for effectuating rotation;
    a spindle supported in said adapter and coupled to said motor;
    a burr attachment removably attached to said adapter comprising:
        an elongated tube,
        a wire shaft supported in said tube and coupled to said adapter for rotation thereof,
        a cutter attached to said wire shaft and extending a predetermined distance from the end of said elongated tube,
        a helically wound and fixed coil wire mounted between the inner surface of said elongated tube and said wire shaft having at least some coils of the wound and fixed coil wire bearing against and surrounding said elongated shaft, each of the coils of the coil wire touching said inner surface of said elongated tube and the outer surface of said wire shaft for minimizing the heat transfer from said wire shaft to said elongated tube,
        a proximal end support attached to a proximal end of said wire shaft and coupled to said adapter and affixed thereto so as to rotate therewith, said proximal end support including:
            a generally cylindrical shaped main body;
            a reduced diameter portion on one end thereof;
            an annular groove formed intermediate the ends thereof;
            an asymmetrical tapered tip portion for entering a passage formed in said adapter and being designed that said tapered tip portion has only one orientation position that allows entrance into said passage; and
            an adapter coupling feature such that the proximal end support is coupled to the adapter at a predetermined orientation position,
        a distal end support coupled to said proximal end support such that said proximal end support rotates independent of said distal end support, and
        said burr attachment being bendable without forming kinks therein;
    a coupling element for mating said burr attachment to said spindle, said coupling element including a detent formed on said proximal end support and including a ball supported in said adapter;
    a cam having a tapered edge formed on an inner diameter thereof, said cam cooperating with the ball for forcing said ball into the detent formed on said proximal end support to couple the burr attachment to said spindle; and
    a spring disposed between a shoulder extending from an outer surface of the spindle and a proximal end of the cam,
    wherein said spring biases said cam toward a distal end of the burr attachment.

2. A medical instrument for burring into small bones in a human patient as claimed in claim 1 wherein said distal end support includes:
    a detent sized and configured to engage a complementary other ball included on said adapter for limiting the position of said burr attachment so that the position of the cutter is always in a predetermined position.

3. A medical instrument for burring into small bones in a human patient as claimed in claim 2 including a second spring wherein said complimentary other ball is biased in a radial position by said second spring.

4. A medical instrument for burring into small bones in a human patient as claimed in claim 1 wherein said distal end support includes grip to allow the burr attachment to be gripped externally to allow the removal of said burr attachment from said adapter.

5. A medical instrument for burring into small bones in a human patient as claimed in claim 1 wherein each of said each of the coils of said coil wire touch said inner surface of said elongated tube and the outer surface of said wire shaft for minimizing the vibrations created by said wire shaft.

6. A medical instrument for burring into small bones in a human patient as claimed in claim 5 wherein said cutter is positioned a predetermined distance from the end of said adapter.

7. A medical instrument for burring into small bones in a human patient as claimed in claim 1 including an end cap mounted on the end of said elongated tube and forming a coil wire retainer for said coil wire for holding said coil wire in place.

8. A medical instrument for burring into small bones in a human patient as claimed in claim 1 wherein said cam includes a main sleeve-like body including the internally formed tapered edge, wherein said tapered edge cooperates with said ball to force said ball radially inward to engage said detent formed on said proximal end support.

9. In combination, an adapter and a bendable burr attachment removably coupled to said adapter,
   said burr attachment having a proximal end and distal end and including:
   a tube,
   a wire shaft disposed in said tube and extending beyond the distal end thereof,
   a cutter mounted on the distal end of said wire shaft and extending beyond said tube,
   a helically wound coil wire surrounding said wire shaft fitted between said wire shaft and said tube assuring that the burr attachment does not kink when bent and the outer diameter of said coil wire bearing against the inner surface of said tube and the inner diameter of said coil spring bearing against the outer diameter of said wire shaft, each of the coils of the coil wire touching said inner surface of said tube and the outer diameter of said wire shaft for minimizing the heat transfer from said wire shaft to said tube,
   a proximal end support attached to a proximal end of said wire shaft and coupled to said adapter and affixed thereto so as to rotate therewith, said proximal end support including;
   a generally cylindrical shaped main body;
   a reduced diameter portion on one end thereof;
   an annular groove formed intermediate the ends thereof;
   an adapter coupling feature such that the proximal end support is coupled to the adapter at a predetermined orientation position, the adapter coupling feature including an asymmetrical tapered tip portion for entering a passage formed in said adapter, said tapered tip having only one orientation position that allows entrance into said passage;
   a distal end support coupled to said proximal end support such that said proximal end support rotates independent of said distal end support;
   said adapter including a main housing having a central axis and defining a cavity having an inlet for receiving the proximal end of said burr attachment and operatively connected to said wire shaft for rotating said cutter;
   a sleeve mounted over said main housing defining a grip adapted to be held by a surgeon for use in a medical procedure;
   a spindle mounted in said cavity being in coincidence with the axis of said housing and coupled to a motor to impart rotational motion thereto;
   said burr attachment having a dimensional profile on the proximal end that matches a complementary dimensional profile on the inlet to said cavity for receiving said burr attachment in only a predetermined orientation;
   a coupling element for mating said burr attachment to said spindle, said coupling element including a detent formed on said proximal end support and including a ball supported in said adapter for engaging the detent to couple said burr attachment and said spindle for powering said cutter,
   a cam having a tapered edge formed on an inner diameter thereof, said cam cooperating with the ball for forcing said ball into the detent formed on proximal end support to couple the burr attachment to said spindle; and
   a spring disposed between a shoulder extending from an outer surface of the spindle and a proximal end of the cam,
   wherein said spring biases said cam toward a distal end of the burr attachment.

10. In combination as claimed in claim 9 wherein said proximal end support includes:
    a flat portion formed on the reduced diameter portion of the main body,
    the asymmetrical tapered tip extending from said flat portion,
    a central partial bore formed internally of said main body for receiving the proximal end of said wire shaft and being affixed thereto so as to rotate therewith.

11. In combination as claimed in claim 10, wherein said distal end support includes:
    a cylindrical main body, said main body having a reduced diameter portion formed on one end dimensioned to fit into a central partial bore formed on the end of said proximal end support to be supported thereby,
    a central bore formed therein and having a reduced diameter portion and a large diameter portion for allowing said wire shaft to pass there through,
    said large diameter portion of said central bore for receiving the proximal end of said coil wire and defining a retainer therefore,
    a flat portion formed on said main body of said distal end support intermediate the ends thereof, and a slot formed on said main body adjacent to said flat portion,
    said adapter including an other ball and a spring urging said other ball radially inward,
    wherein said other ball fits into said slot for orienting said burr attachment and said adapter to precisely position said cutter to the end of said adapter.

12. In combination as claimed in claim 11 including a grip formed on one end of said distal end support remote from said smaller diameter portion for allowing the removal of said burr attachment from said adapter.

13. In combination as claimed in claim 9 wherein said cam includes a sleeve-like main body including the tapered edge, said tapered edge cooperating with said ball for driving said ball radially inward in said adapter to engage said detent.

14. In combination as claimed in claim 9 wherein the helix of said coil wire is in a direction that forces a lubricant on the tip of said tube to migrate toward the proximal end of said coil wire to provide lubrication thereto.

15. In combination as claimed in claim 9 wherein said coil wire extends from the tip of said tube to a juncture point intermediate the ends thereof and a second coil wire that is larger than said coil wire extends from the proximal end of said coil wire to the end of said tube.

16. A curved burr attachment including a burr attachment and an adapter rotatably driven by a motor wherein said burr attachment is coupled to said adapter for rotational motion by the insertion of said burr attachment into said adapter and removable from said adapter by pulling said burr attachment to decouple and remove the burr attachment from said adapter,
    said burr attachment including a tube, a wire shaft supported in said tube having a proximal end support and a distal end support, a cutter attached to said wire shaft, a helically wound coil wire surrounding said shaft and disposed between said wire shaft and said tube, wherein the outer periphery of each of said coils of said coil wire touch the inner surface of said tube and the inner periphery of each of said coils of said coil wire touch the outer surface of said wire shaft, said adapter including a main housing defining a cavity, a spindle adapted to be driven by a drill motor disposed in said cavity and having a partial bore formed on one end thereof, said proximal end support being affixed to a proximate end of said wire shaft and coupled to said adapter and affixed to rotate therewith, said proximal end support being disposed in said partial bore of said spindle, said proximal end support including;

a generally cylindrical shaped main body;

a reduced diameter portion on one end thereof;

an adapter coupling feature such that the proximal end support is coupled to the adapter at a predetermined orientation position, said coupling feature including an annular groove formed on said proximal end support, said coupling feature also include an asymmetrical tapered tip portion for entering a passage from in said adapter and being designed such that said tapered tip portion has one orientation position that allows entrance into the passage;

said distal end support coupled to said proximal end support such that said proximal end support rotates independently of said distal end support, a sleeve-shaped cam having tapered inner surface at its forward end and biased on one end by a spring, balls freely disposed in holes formed in said spindle and between the inner surface of said main housing, said proximal end support having a flat portion and said annular groove formed adjacent thereto such that movement of said burr attachment into said cavity causes said balls to engage said sleeve-shaped cam and urge it rearwardly to compress said spring, when the force of said spring reaches a predetermined value it will force said sleeve-like cam toward the distal end so that said tapered inner surface engages said balls to radially force said balls into said annular groove of said proximal end support to couple said spindle thereto to rotate said wire shaft and automatically lock said burr attachment in place in said adapter.

17. A curved burr attachment including a burr attachment and an adapter as claimed in claim 16 comprising an other ball mounted in a slot formed in said main housing, a spring urging said other ball radially inward, said distal end support having a detent, said other ball fitted into said detent of said distal end support when said burr attachment is inserted into said cavity so as to precisely locate said cutter in a predetermined position relative to the end of said adapter.

* * * * *